United States Patent [19]
Holland

[11] Patent Number: 5,827,523
[45] Date of Patent: Oct. 27, 1998

[54] UNIVERSAL TOPICAL ANTISEPTIC FIRST AID SPRAY

[76] Inventor: Dennis A. Holland, 16461 Big Oak Bay Rd., Tyler, Tex. 75707

[21] Appl. No.: 848,666

[22] Filed: Apr. 29, 1997

[51] Int. Cl.⁶ .............................. A01N 25/00; A61K 7/40
[52] U.S. Cl. ............................................. 424/405; 424/400
[58] Field of Search .................................... 424/400, 405, 424/78.05, 78.06, 78.07

[56] References Cited

U.S. PATENT DOCUMENTS

| | | |
|---|---|---|
| 4,110,428 | 8/1978 | Kuhn et al. . |
| 4,265,905 | 5/1981 | Shen et al. . |
| 4,963,591 | 10/1990 | Fourman et al. . |
| 5,512,200 | 4/1996 | Garcia . |

*Primary Examiner*—Thurman K. Page
*Assistant Examiner*—Brian K. Seidleck

[57] ABSTRACT

This first aid spray is different from any other first aid spray. It has an indefinite shelf life, is safe for the environment, and is unaffected by heat or cold. It doesn't use conventional methods to accomplish its objectives of relieving pain and, reducing swelling, and allowing the skin to neutralize.

2 Claims, No Drawings

UNIVERSAL TOPICAL ANTISEPTIC FIRST AID SPRAY

BACKGROUND OF THE INVENTION

This invention relates to a convenient topical first spray needed to save time and money, and safely correct problems.

In this day and time it is more and more important that what is used to solve problems shouldn't add different elements to the problem.

Previous and current conventional first aid sprays are ineffective in allowing the skin to repair itself, and are selective in use. They quite often contain materials that are ultimately harmful to the individual using them and to the environment, and have a limited shelf life. Some of them contain aerosol gases that often run out before the material, and such gases can be dangerous around flame and heat.

BRIEF SUMMARY OF THE INVENTION

This invention is designed to allow for use in a manner that will not add harmful elements to the environment or cause adverse side effects when used.

The spray is easy and simple to use on any problem with the skin. It is safe on any part of the body and is hypoallergenic. Because the spray can be used on a variety of skin problems, and has an indefinite shelf life, it is cost effective to those using it.

DETAILED DESCRIPTION OF THE INVENTION

This first aid spray relieves pain from burns caused by heat, fire, chemicals, creosote, sunburn, radiation therapy, or wind burn. It stops blistering, redness, and scarring from all burns.

It relieves irritation, pain, swelling, itching, blistering and redness from insect bites and stings that include: fire ants, all other ants, spiders, fleas, chiggers (red bugs), buffalo gnats, mosquitos, scorpions, bees, wasps, and all other insects.

Contains bacteriastats that effectively control bacterial growth on the skin, that will ultimately lead to odor and infection. Control of bacteria on the skin will help avoid contamination of food products.

This spray relieves symptoms of heat rash, jock itch and rash, athletes foot, chicken pox, shingles, psoriasis, eczema, cold sores, fever blisters, and jelly fish stings.

It will relieve irritation, itching, swelling, and blistering from poison ivy, poison oak, poison sumac, bull neetle, and all other poison plants.

This spray has an indefinite shelf life and does not expire. It is unaffected by heat or cold, and is non-flammable. It contains no oils, or grease, and will not leave a residue on the skin. It does not leave a bad odor and will not stain skin or clothing.

It is biodegradable and hypoallergenic and will not harm the environment.

The following is the formulation of a 50 gallon mixture:

| Ingredient | Quantity |
|---|---|
| Purified Water (Deionized) | 166,000 ml |
| 50-HB-2000 | 6,400 ml |
| Ethyl Alcohol (SDA-40 190 Proof-95% Alcohol) | 15,850 ml |
| Cresylic Acid | 140 Drops |
| Hydrochloric Acid | 2,000 ml |
| Allantoin | 500 Grams |
| DL Panthenol | 500 Grams |
| PHENOSEPT 25P | 2,000 ml |

Step One: Add 122,000 ml Deionized Water

Step Two: Add 6,400 ml 50-HB-2000 [Union Carbide lists this ingredient as Polyalkylene Glycol]

Step Three: Predissolve 500 Grams of 11a in 12,000 ml Ethyl Alcohol and add at this point Step Four: Add 40,000 ml Deionized Water Step Five: Predissolve 2,000 ml of PHENOSEPT 25P [NIPA Hardwicke lists this ingredient as 75% Phenoxy Isopropanol & 25% chloroxylenol]in 5,850 ml of Ethyl Alcohol and add at this point Step Six: Add 140 drops of Cresylic Acid to the first 1000 ml of of Phenoxy Isopropanol & Chloroxylenol in Step Five.

Step Seven: Add 2,000 ml of Hydrochloric Acid

Step Eight: Add 6,000 ml Deionized Water

Step Nine: Add 500 Grams of DL Panthenol

Step Ten: Add 2,000 ml Phenoxy Isopropanol & Chloroxylenol

Note: This product must maintain a Ph of about One (1). This can be accomplished using the two acid ingredients.

While the above formula is optimum, it can be altered as much as 40% by negative or positive with a variance in the Ph from 0.90 through 1.05 and still be effective as the same invention.

This spray is simple and easy to use, because it is held six to eight inches from the affected area and the pump is pushed down. It works more efficiently because there are no gases involved and the product is usable until empty of fluid.

I claim:

1. A topical composition, which when applied to the skin, provides an instant cooling effect in the skin, consisting of: Deionized Water, Polyalkylene Glycol, Ethyl Alcohol, Cresylic Acid, Hydrochloric Acid, Allantoin, DL Panthenol, Phenoxy Isopropanol and Chloroxylenol, with a pH of about 1.

2. A method of treating topical pain from burns; itching from insect bites; the discomfort of dry and irritated skin; infection by eliminating bacterial growth on burns, cuts, and bites, consisting of topically administering the composition of claim 1 by spraying it on the skin.

* * * * *